United States Patent
Pekander

(10) Patent No.: US 10,307,073 B2
(45) Date of Patent: Jun. 4, 2019

(54) ECG SENSOR WITH CAPACITIVE DEFIBRILLATION PROTECTION

(71) Applicant: General Electric Company, Schenectady, NY (US)

(72) Inventor: Otto Valtteri Pekander, Helsinki (FI)

(73) Assignee: General Electric Company, Schenectady, NY (US)

(*) Notice: Subject to any disclaimer, the term of this patent is extended or adjusted under 35 U.S.C. 154(b) by 289 days.

(21) Appl. No.: 15/387,276

(22) Filed: Dec. 21, 2016

(65) Prior Publication Data

US 2018/0168475 A1 Jun. 21, 2018

(51) Int. Cl.
*A61B 5/04* (2006.01)
*A61B 5/0428* (2006.01)
(Continued)

(52) U.S. Cl.
CPC ........ *A61B 5/04284* (2013.01); *A61B 5/0408* (2013.01); *A61B 5/04017* (2013.01); *A61B 5/0424* (2013.01); *A61N 1/3925* (2013.01); *A61B 5/0402* (2013.01); *A61B 5/08* (2013.01); *A61B 2562/0214* (2013.01)

(58) Field of Classification Search
CPC ............ A61B 5/04284; A61B 5/04017; A61B 5/0424; A61B 5/0408; A61B 2562/0214; A61B 5/08; A61B 5/0402; A61N 1/3925
See application file for complete search history.

(56) References Cited

U.S. PATENT DOCUMENTS 6,377,845 B1 4/2002 Kinast
6,496,705 B1 12/2002 Ng et al.
(Continued)

FOREIGN PATENT DOCUMENTS

EP 1359842 B1 5/2009
EP 2559280 A1 2/2013
(Continued)

OTHER PUBLICATIONS

International Search Report and Written Opinion for International Application No. PCT/US2017/066401 dated Feb. 23, 2018. 10 pages.
(Continued)

*Primary Examiner* — Rex R Holmes
(74) *Attorney, Agent, or Firm* — Andrus Intellectual Property Law, LLP

(57) ABSTRACT

A patient monitoring system includes a capacitive electrode connectable to a patient to detect an output signal and a signal generator unit that transmits a carrier signal to the capacitive electrode, the carrier signal having a carrier frequency and a carrier amplitude. The patient monitoring system further includes an amplifier unit that amplifies the output signal detected by the capacitive electrode to generate an amplified output signal. A gain determination module in the patient monitoring system determines an output amplitude of a carrier frequency portion of the amplified output signal, and determines a system gain based on a comparison between the output amplitude and the carrier amplitude. A voltage determination module in the patient monitoring system filters the output signal to isolate a physiological signal detected from the patient, and determines a voltage of the physiological signal based on the system gain.

20 Claims, 6 Drawing Sheets

(51) Int. Cl.
*A61B 5/0408* (2006.01)
*A61B 5/0424* (2006.01)
*A61N 1/39* (2006.01)
*A61B 5/0402* (2006.01)
*A61B 5/08* (2006.01)

(56) References Cited

U.S. PATENT DOCUMENTS

| | | |
|---|---|---|
| 6,749,566 B2 | 6/2004 | Russ |
| 7,390,299 B2 | 6/2008 | Weiner et al. |
| 8,475,368 B2 | 7/2013 | Tran et al. |
| 2004/0173003 A1 | 9/2004 | Ibane |
| 2006/0136768 A1 | 6/2006 | Liu et al. |
| 2006/0284621 A1 | 12/2006 | Doi |
| 2008/0284599 A1 | 11/2008 | Zdeblick |
| 2009/0318818 A1 | 12/2009 | Whitaker et al. |
| 2010/0168605 A1 | 7/2010 | Aarts |
| 2011/0066051 A1 | 3/2011 | Moon |
| 2011/0145894 A1 | 6/2011 | Morchon et al. |
| 2012/0068855 A1 | 3/2012 | Matsumura |
| 2012/0108917 A1 | 5/2012 | Libbus et al. |
| 2013/0053674 A1 | 2/2013 | Volker |
| 2013/0109927 A1 | 5/2013 | Menzel |
| 2013/0289376 A1 | 10/2013 | Lang |
| 2013/0337842 A1 | 12/2013 | Wang et al. |
| 2014/0187883 A1 | 7/2014 | Lisogurski |
| 2014/0200469 A1 | 7/2014 | Bocko et al. |
| 2015/0116130 A1 | 4/2015 | Grubis |

FOREIGN PATENT DOCUMENTS

| | | |
|---|---|---|
| EP | 1881784 B1 | 10/2013 |
| WO | 2011/007292 A1 | 1/2011 |
| WO | 2014027273 A1 | 2/2014 |
| WO | 2015/075692 A1 | 5/2015 |
| WO | 2016/044933 A1 | 3/2016 |

OTHER PUBLICATIONS

Pending U.S. Appl. No. 14/586,393, filed Dec. 30, 2014, "Common Display Unit for a Plurality of Cableless Medical Sensors", Muuranto.
Radius-7 brochure, Masimo, admitted prior art.
IntelliVue Cableless Measurement brochure, Philips, Jun. 2013.
http://electronicdesign.com/power/lightning-bolts-defibrillators-and-protection-circuitry-save-lives.
Soundarapandian et al., "Analog Front-End Design for ECG Systems Using Delta-Sigma ADCs", Texas Instruments, SBAA160A, Mar. 2009, Revised Apr. 2010.
Torres, Bernat Albet., "Wireless System for the Measurement of Bioelectric Signals using Capacitive Electrodes", Universitat Politecnica de Catalunya.
International Search Report and Written Opinion issued in connection with corresponding PCT Application No. PCT/US2017/067193 dated Apr. 9, 2018.

ECG SENSOR WITH CAPACITIVE DEFIBRILLATION PROTECTION

BACKGROUND

This disclosure generally relates to medical monitoring systems and devices, and more specifically to patient monitors using one or more capacitive electrodes.

Electrocardiograms (ECGs) are graphic depictions of electrical activity in the heart. ECGs are produced by electrocardiographs which are available as stand alone devices, portable devices, and/or as integrated functions in various types of multi-vital sign monitoring devices. ECGs are depicted by time (ms) versus voltage (mV) and typically are represented as a waveform. The typical five important aspects, or portions, of an ECG waveform are the P wave, QRS complex (represented as the combination of the Q, R, and S waves respectively), and T wave. The less frequently seen sixth portion is a U wave. The data produced from the graphical depictions are useful in diagnosis of patients to determine what, if any, and the extent to which heart-related problems exist in a patient. Respiration monitors are also available that use chest electrodes that are similar or identical to ECG electrodes that are similar or identical to ECG electrodes. For example, respiration rate measurement may be determined using impedance pneumography, where a high-frequency AC current is passed between at least two electrodes, including a driving electrode and a receiving electrode, on the patient's chest and an impedance between the electrodes is determined. Respiration is then monitored according to the changing impedance values as the patient breathes.

Both electrocardiographs and respiration monitors must have protection circuitry to protect the electronics of those devices from high voltage exposure due to operation of a defibrillator on a patient to which the monitoring devices are connected. Patients experiencing sudden cardiac arrest are treated with a defibrillation shock to the chest. The defibrillation shock is typically in the range of 3 to 5 kV and 50 amps, and typically lasts between 5 and 20 ms. Such a high voltage and current are necessary in order to stop the patient's heart from unproductive fluttering (fibrillating) and to allow the heart to restart effective pumping of blood. Typically, respiration monitors and electrocardiographs are separate from the defibrillator device, and the chest electrodes and lead wires are connected to the patient when the defibrillator delivers the shock. Thus, the electrocardiograph and respiration monitors must withstand the significant voltage and current of the defibrillation and continue working properly.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a patient monitoring system includes a capacitive electrode connectable to a patient to detect an output signal and a signal generator unit that transmits a carrier signal to the capacitive electrode, the carrier signal having a carrier frequency and a carrier amplitude. The patient monitoring system further includes an amplifier unit that amplifies the output signal detected by the capacitive electrode to generate an amplified output signal. A gain determination module in the patient monitoring system determines an output amplitude of a carrier frequency portion of the amplified output signal, and determines a system gain based on a comparison between the output amplitude and the carrier amplitude. A voltage determination module in the patient monitoring system filters the output signal to isolate a physiological signal detected from the patient, and determines a voltage of the physiological signal based on the system gain.

One embodiment of a method of patient monitoring using at least one capacitive electrode includes generating a carrier signal at a carrier frequency and a carrier amplitude and transmitting the carrier signal to the capacitive electrode. An output signal is received from the capacitive electrode, which is then amplified to create an amplified output signal. An output amplitude of a carrier frequency of the amplified output signal is determined, and the output amplitude is compared to the carrier amplitude to determine a system gain. The output signal is then filtered to isolate a physiological signal of the patient, and a voltage of the physiological signal is determined based on the system gain.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Figure 1:
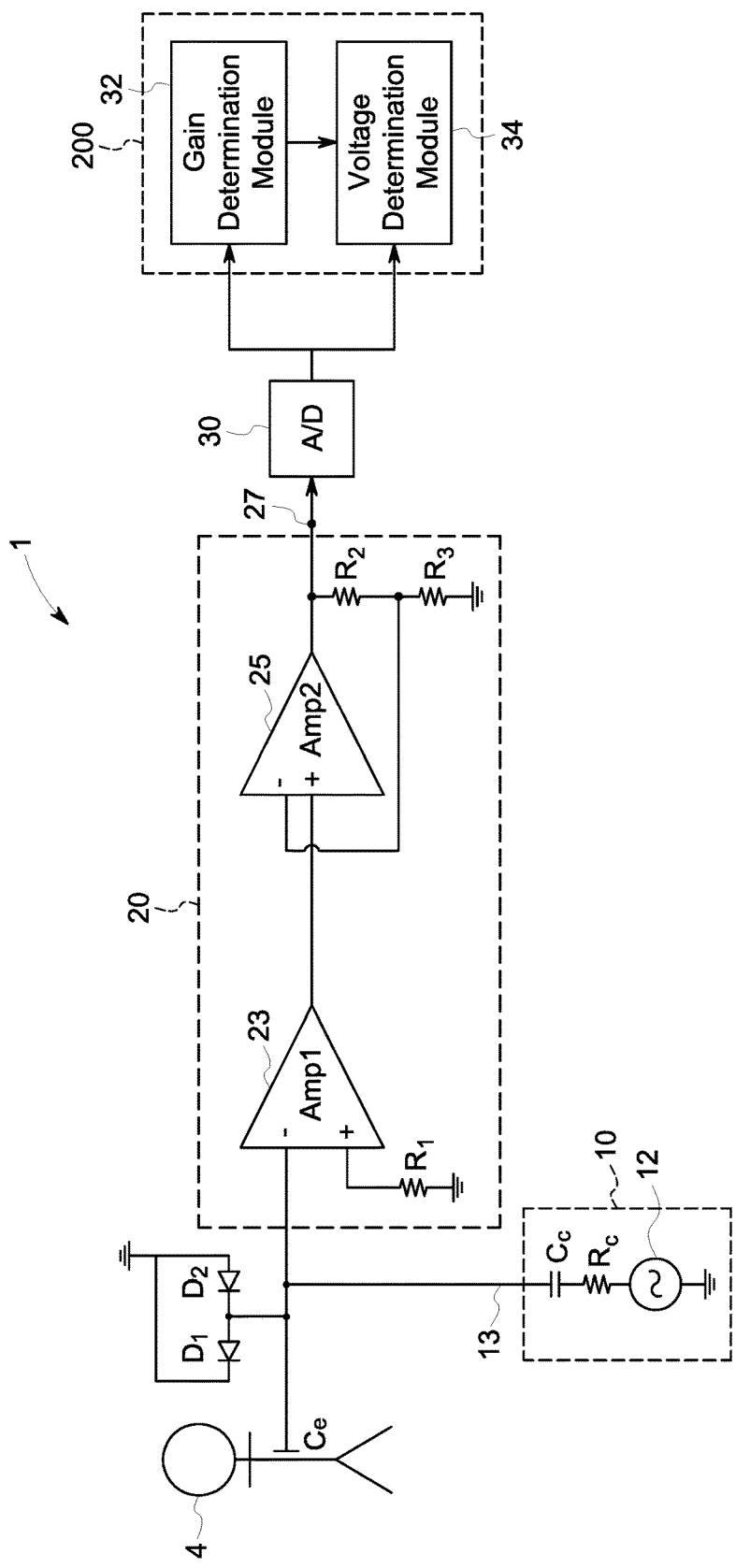
FIG. 1 depicts one embodiment of a patient monitoring system having a capacitive electrode.

As described above, electrocardiographs and respiration monitors must be configured to withstand the high voltage defibrillation pulses, which are on the order of 3 to 5 kV and 50 amps and last for 5 to 20 ms (which is a long time for electronic components to survive such high voltage). Thus, such monitoring devices are typically provided with defibrillation protection circuitry at their inputs which is designed to absorb the energy of the high voltage pulse before it reaches the sensitive electronics. Defibrillation protection in electrocardiograph and respiration monitoring devices has traditionally been implemented with resistors, which are large and expensive because they must be designed to cope with huge defibrillation power surges. Additionally, resistive components introduce thermal noise. For example, the energy travelling through an average 10 kiloohm resistor from a 5 kilovolt defibrillation pulse can cause the resistor to reach very high temperatures, such as internal temperatures reaching 200° Celsius or higher. This significant heating of the resistor causes it to break down.

The present inventor has recognized that the use of capacitive, or more generally reactive, impedance in place of or in addition to such passive resistive components enables the use of high impedance levels without inherent noise issues. Further, the present inventor has recognized that capacitive electrodes could be utilized to protect against the defibrillation pulse. In addition to the selective isolating properties of using capacitive electrodes, the inventor has recognized that the use of capacitive electrodes has the added benefit of avoiding conductive gels and pastes, such as silver/silver chloride gel, typically used on galvanic conduction chest electrodes that are often irritating to patient's skin. Such irritation can be especially problematic if the electrodes are to be worn by the patient over a long period of time, or if the patient has particular sensitivity or allergy to the conductive pastes and gels utilized in conductive surface electrodes.

Capacitive electrodes solve the aforementioned defibrillation resistor problems; however, the inventors have recognized that most capacitive sensor topologies suffer from variance of the gain which is proportional to the capacitive coupling strength to the skin. The inventors have recognized that this problem is severe because the capacitance between the electrode and the patient's skin, and thus the capacitive coupling strength, can vary greatly, and such changes can happen quite quickly. For example, the capacitance between the electrode and the patient can change instantaneously due to a patient's movement, which can change the distance between the plate of the capacitive electrode and the patient, for example. Additionally, the capacitance of the electrode to the patient can change based on changes in the patient's skin chemistry, such as due to sweating, or by the presence of a hair between the capacitive plate of the electrode and the patient's skin. Additionally, in certain embodiments it is advantageous to place the capacitive electrodes over an insulating element between the patient's skin and the capacitive plate of the electrode, such as over a shirt worn by the patient. This leads to an even greater tendency for changes in the capacitance between the capacitive electrode and the patient.

The changes in coupling capacitance change the gain of the output signals, either the noise level or the signal gain is modulated by the absolute capacitance value between the capacitive electrode and the skin. Accordingly, variation in that capacitance value provides challenges for patient monitoring. Namely, it is important to know the gain applied to the physiological signals measured from the patient's body so that the amplitude of those signals can be accurately ascertained.

In view of the beneficial properties of capacitive electrodes and the problems and challenges with relevant prior art systems that use capacitive electrodes, the inventor developed the disclosed system and method which transmits a carrier signal to the input of the capacitive electrodes and measures the amplification behavior of the system based on measurement at the frequency of the carrier signal. Specifically, the inventor recognized that the carrier signal, which generally has a frequency well above the relevant frequencies of the physiological signals desired to be measured, will be attenuated by the capacitive connection between the capacitive electrode and the patient, which is due to changes in the capacitive path to ground. This same attenuating effect will occur to the physiological signals. Thus the gain variance due to changes in capacitance between the capacitive electrode and the patient can be accounted for by monitoring the behavior of the carrier signal, or the signal at the carrier frequency.

Assuming that the amplification circuit behaves the same at the low frequencies of the physiological signal as the high frequencies of the carrier signal, then the gain variance of the physiological signal can be ascertained by determining the gain of the carrier signal at the output of the amplifier amplifying the output signals detected by the capacitive electrode. Namely, the system gain due to the capacitive electrode and amplification circuitry can be determined by comparing the amplitude of the output signal to the amplitude of the carrier signal at the time of input, and more specifically by comparing the amplitude of the carrier frequency portion of the output signal to the amplitude of the carrier signal at input. In an embodiment where the amplification circuit behaves the same at the relevant frequency ranges, the gain variance of the physiological signal can be ascertained by solving for the capacitance of the capacitive electrode. Namely, where the gain of the amplification circuit is known and the capacitance to ground is known, one can solve for the value of the sensor-to-skin capacitance.

FIG. 1 depicts one embodiment of a patient monitoring system 1 having the above described features and aspects. The system 1 generally comprises a capacitive electrode $C_e$ capacitively coupled to a patient 4 to detect physiological signals therefrom. The system 1 further includes a signal generator unit 10 that generates and transmits a carrier signal to the capacitive electrode. The carrier signal has a frequency, referred to herein as a carrier frequency, and an amplitude, referred to herein as the carrier amplitude. The system 1 further includes an amplifier unit 20 that transfers the high impedance signal to low impedance and amplifies the output signal. In the depicted embodiment, the amplified output signal is digitized by an analog-to-digital converter 30, which may be part of an analog front end. The amplified and digitized output signal is then passed to a gain determination module 34 that determines a gain for the amplifier unit 20 and the capacitive electrode $C_e$, which in the depicted embodiment is the system gain. The voltage determination module 34 then utilizes the system gain determined by the gain determination module 32 to determine a voltage of the physiological signal. The capacitive electrode $C_e$ may be any capacitive electrode that uses capacitance for bioelectric measurement. A person having ordinary skill in the art will know that several different capacitive electrodes already exist in the market. For example, the capacitive electrode may be the QUASAR IBE by Quantum Applied Science and Research, Inc. of San Diego, Calif. As described above, the capacitive electrode $C_e$ may be fixed directly to the patient's skin, and thus may touch the patient's skin, or may be separated from the patient's skin by a material, such as a garment or a band to which the capacitive electrode may be fixed.

A signal generator unit 10 generates a carrier signal that is transmitted to the capacitive electrode $C_e$. The carrier signal has a relatively small amplitude that is safe for delivery to a patient. To provide just one example, the carrier signal may be a 1 kHz, 1 mV signal. To provide just one example, the resistor $R_c$ may be a 10 kiloohm resistor. In the depicted embodiment, the signal generator unit includes an AC signal generator 12 placed in series with the resistor $R_c$ and a capacitor $C_c$. The capacitor $C_c$ acts as a high pass filter that removes any DC element and low frequency noise from the carrier signal, which is outputted from the signal generator unit 10 at node 13. The carrier signal has a carrier frequency that is generally above the frequency of the physiological signals intended to be measured by the system 1. Thus, in an ECG application, for example, the carrier frequency may be above 150 Hz, and preferably well above that frequency so that the carrier signal can be easily filtered out without disturbing the recorded physiological signal. For example, the carrier frequency may be in the range of 1 kHz or higher, such as 10 kHz or 50 kHz. The capacitance of the capacitor $C_c$ is provided to appropriately filter out the low frequency noise below the carrier frequency. To provide just one exemplary embodiment, the capacitor $C_c$ may be a 10 pF capacitor.

The carrier signal is transmitted to the capacitive plate of the capacitive electrode $C_e$. An output signal, which includes the carrier signal and physiological signals measured from the patient, is then transmitted to the amplifier unit 20. A set of diodes $D_1$ and $D_2$ are provided in the depicted arrangement to maintain a DC level of the output signal within boundaries that the amplifier unit can handle. The diodes $D_1$, $D_2$ leak charge out of the system 1 if the DC baseline drifts too far away from zero in either the positive or negative direction.

In the depicted embodiment, the amplifier unit 20 includes a first amplifier 23 and a second amplifier 25. The purpose of the first amplifier 23 is to turn the tiny current of the output signal emerging from the capacitive electrode $C_e$ into a voltage signal. As the DC baseline of the output signal is prone to drift, small gains are applied at the first amplifier stage, which may be only a gain of one or two. Any of various elements may serve this purpose, and thus may comprise the first amplifier 23. In one embodiment, the first amplifier 23 may be as simple as a single transistor, such as a junction gate field-effect transistor (JFET). Alternatively, the first amplifier 23 may be an ultra low input bias current instrumentation amplifier, such as an INA116UAI Texas Instruments Inc. of Dallas, Tex. The first amplifier 23 may amplify the output signal with reference to ground, or other common reference, through resistor $R_1$. In other embodiments, the first amplifier 23 may utilize negative feedback that applies a portion of the output voltage from the amplifier to the inverting input.

In the depicted embodiment, the amplifier unit 20 includes a second amplifier 25 that provides significant amplification to the signal emerging from the first amplifier 23. Any of various types of amplifiers may be utilized as the second amplifier 25, which in the depicted embodiment is exemplified as an operational amplifier (OP-AMP) connected in a closed-loop feedback arrangement, where the value of the resistors $R_2$ and $R_3$ in the voltage divider determines the closed-loop gain of the second amplifier 25. In one embodiment, the gain of each of the amplifiers 23 and 25 is known, and thus the gain of the amplifier unit 20 is also known, which is referred to herein as the known amplifier gain.

The amplifier unit 20 provides an amplified output signal at node 27. In various embodiments, additional circuit elements may be present, such as filters and/or other amplification elements. For example, the amplified output signal may be provided to an analog front end with various signal processing circuit elements, which will be known to a person having ordinary skill in the relevant art. The amplified output signals are digitized by the analog-to-digital converter 30. In certain embodiments, filter elements may be present to separate the signal into a high frequency portion representing the carrier frequency portion of the amplified output signal and the lower frequency portion containing the physiological signals measured by the patient. The filtered high frequency and low frequency portions may then be separately digitized and passed to the signal processing modules similarly to that described below.

In the depicted embodiment the digitized and amplified output signal is passed to each of a gain determination module 32 and a voltage determination module 34. In the depicted embodiments, the modules are digitally implemented via execution of software instructions on a processor; however, in other embodiments certain aspects of the module may be carried out in analog form, such as by analog filtering. The gain determination module 32 generally isolates the carrier frequency aspect of the amplified output signal, such as by utilizing a high pass filter or a band pass filter to isolate the signal portion at the carrier frequency. The gain determination module 32 further includes instructions that determine an output amplitude of the carrier frequency portion of the amplified output signal, and then to determine the system gain based on a comparison between the output amplitude and the original carrier amplitude. For example, the system gain may be equal to the output amplitude divided by the carrier amplitude.

The system gain is then passed to the voltage determination module which utilizes the system gain to determine a voltage of the physiological signal measured by the capacitive electrode $C_e$. For example, the voltage determination module may isolate the physiological signal by utilizing a low pass filter designed to isolate the frequency range at which the targeted physiological signal is found. To provide just one example relevant to an embodiment where the physiological monitor is an ECG device, the voltage determination module may apply a low pass filter with a cut off frequency of 150 Hz to isolate the relevant cardiac signals. In other embodiments, the cut off frequency of the filter may be higher or lower than 150 Hz. The voltage of the physiological signal is then determined based on the system gain, such as by dividing the amplitude of the physiological signal by the system gain.

It will be understood by a person having ordinary skill in the art reviewing this disclosure that the patient monitoring system 1 may include any number of capacitive electrodes $C_e$, and that a carrier signal will be transmitted to each of the capacitive electrodes $C_e$ in the system 1, which may be by separate signal generator units for each capacitive electrode $C_e$, or by signal generator units 10 commonly shared between two or more capacitive electrodes $C_e$.

Aspects of the disclosure are described herein in terms of functional and/or logical block components and various processing steps. It should be appreciated that such block components, including the "modules" described herein, may be realized by any number of hardware, software, and/or firmware components configured to perform the specified functions. For example, an embodiment may employ various integrated circuit components, e.g., memory elements, digital signal processing elements, logic elements, look-up tables, or the like, which may carry out a variety of functions under the control of one or more processors or other control devices. As used herein, the term module may refer to software code, and also may include an application-specific integrated circuit (ASIC), an electronic circuit, a combinational logic circuit, a field programmable gate array (FPGA), a processor (shared, dedicated, or group) that executes the code, or other suitable components that provide the described functionality, or a combination of some or all of the above, such as in a system-on-chip. The term module may also include memory (shared, dedicated, or group) that stores code executed by the processor. The term code, as used herein, may include software, firmware, and/or microcode, and may refer to programs, routines, functions, classes, and/or objects. The term shared, as used above, means that some or all code from multiple modules may be executed using a single (shared) processor. In addition, some or all code to be executed by multiple different processors may be stored by a single (shared) memory. The term group, as used above, means that some or all code comprising part of a single module may be executed using a group of processors. Likewise, some or all code comprising a single module may be stored using a group of memories.

Figure 2:
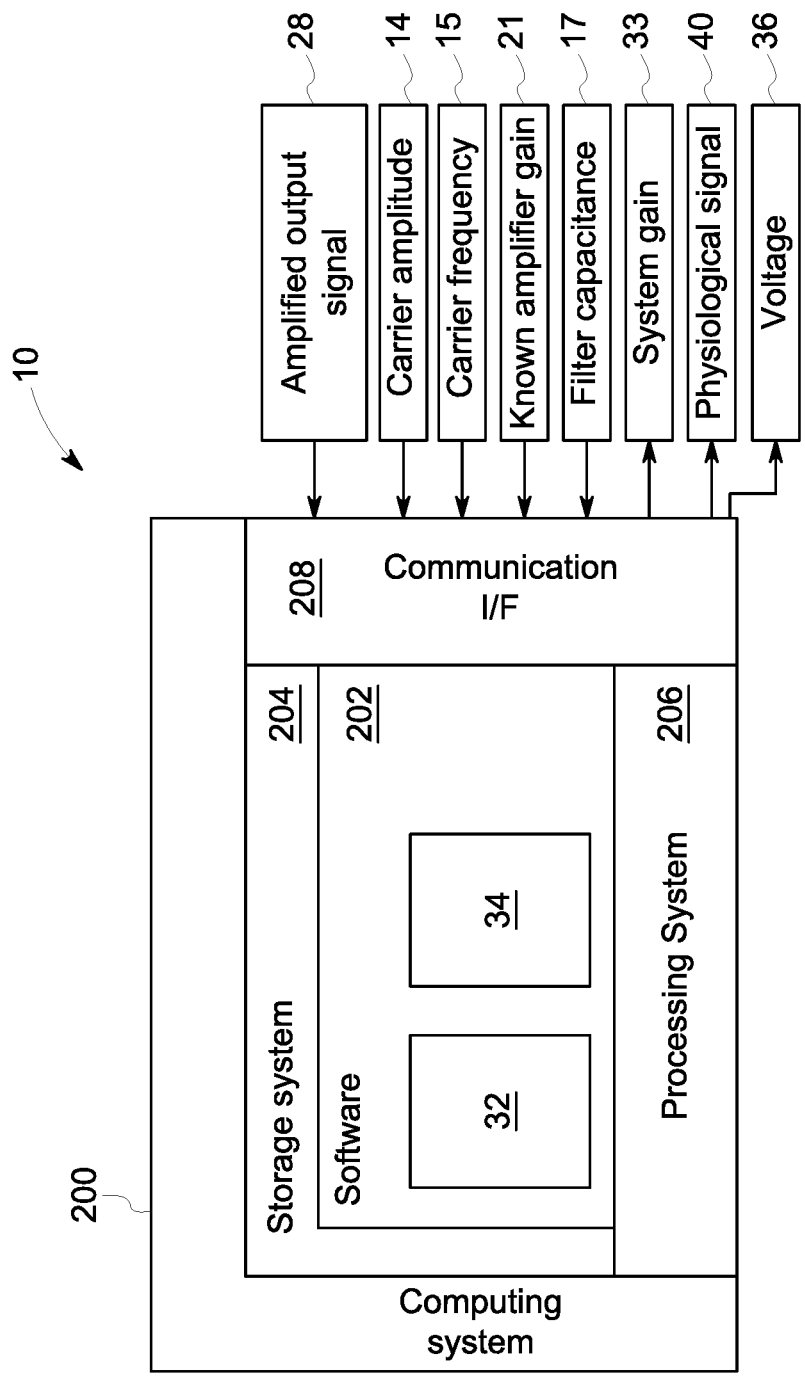
FIG. 2 depicts one embodiment of an exemplary computing system that may be included in the patient monitoring system having one or more capacitive electrodes.

FIG. 2 provides a system diagram of one exemplary computing system 200 for an embodiment of the patient monitoring system 10, the computing system 200 having a gain determination module 32 and a voltage determination module 34, which in the depicted embodiment are applications within the software 202. For example, the computing system 200 may be housed within a data acquisition device that is part of the patient monitoring system 1, which may be housed at or near the capacitive electrode $C_e$, or the computing system 200 may be housed in a bed-side central patient monitoring device. The computing system 200 includes a processing system 206, storage system 204, software 202, and a communication interface 208. The processing system 206 loads and executes software 202 from the storage system 204, including the gain determination module 32 and the voltage determination module 34. Each of the modules 32 and 34 include computer-readable instructions that, when executed by the computing system 200 (including the processing system 206), direct the processing system 206 to operate as described in herein in further detail, including to execute the steps to determine the system gain 33 and the voltage 36 of the physiological signal 40 based on the amplified output signal 28 received from the amplifier unit 20.

Although the computing system 200 as depicted in FIG. 2 includes one software 202 encapsulating one gain determination module 32 and one voltage determination module 34, it should be understood that a single software element having a single module may provide the same operation— i.e., the instructions described as being part of the gain determination module 32 and the voltage determination module 34 may be provided in a single set of software instructions called and executed on the processing system 206. Likewise, the instructions described as being part of the gain determination module 32 and the voltage determination module 34 may be divided among more than two modules, housed in multiple software 202 elements. Similarly, while description as provided herein refers to a computing system 200 and a processing system 206, it is to be recognized that implementations of such systems can be performed using one or more processors, which may be communicatively connected, and such implementations are considered to be within the scope of the description.

The processing system 206 includes a processor, which as described above may be a microprocessor, a general purpose central processing unit, and application-specific processor, a microcontroller, or any other type of logic-based device. The processing system 206 may also include circuitry that retrieves and executes software 202 from storage system 204. Processing system 206 can be implemented within a single processor but can also be distributed across multiple processing devices or sub-systems that cooperate in executing program instructions.

The storage system 204, can comprise any storage media, or group of storage media, readable by processing system 206, and capable of storing software 202. The storage system 204 can include volatile and non-volatile, removable and non-removable media implemented in any method or technology for storage of information, such as computer-readable instructions, data structures, program modules, or other data. Storage system 204 can be implemented as a single storage device but may also be implemented across multiple storage devices or sub-systems.

Examples of storage media include random access memory, read only memory, optical discs, flash memory, virtual memory, and non-virtual memory, magnetic sets, magnetic tape, magnetic disc storage or other magnetic storage devices, or any other medium which can be used to store the desired information and that may be accessed by an instruction execution system, as well as any combination or variation thereof, or any other type of storage medium. Likewise, the storage media may be housed locally with the processing system 206, or may be distributed in one or more servers, which may be at multiple locations and networked, such as in cloud computing applications and systems. In some implementations, the storage media can be a non-transitory storage media. In some implementations, at least a portion of the storage media may be transitory.

The communication interface 208 interfaces between the elements within the computing system 200 and external devices, such as the amplifier unit 20 and/or the signal generation unit 10. Additionally, the communication interface 208 may communicate the output values from the gain determination module 32 and the voltage determination module 34, such as the system gain 33, the physiological signal 40, and/or the voltage 36 of the physiological signal, to other aspects of the patient monitoring system 1, such as to a user interface for display to a clinician and/or to a central computing system of a medical facility for storage in the patient's 4 medical record.

Figure 3:
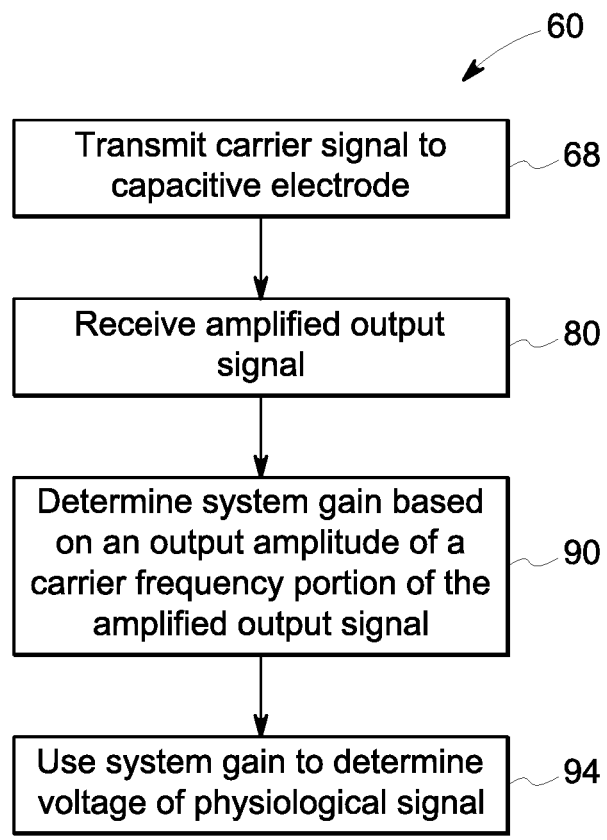
FIG. 3 depicts one embodiment of a method of patient monitoring using at least one capacitive electrode.
Figure 4A:
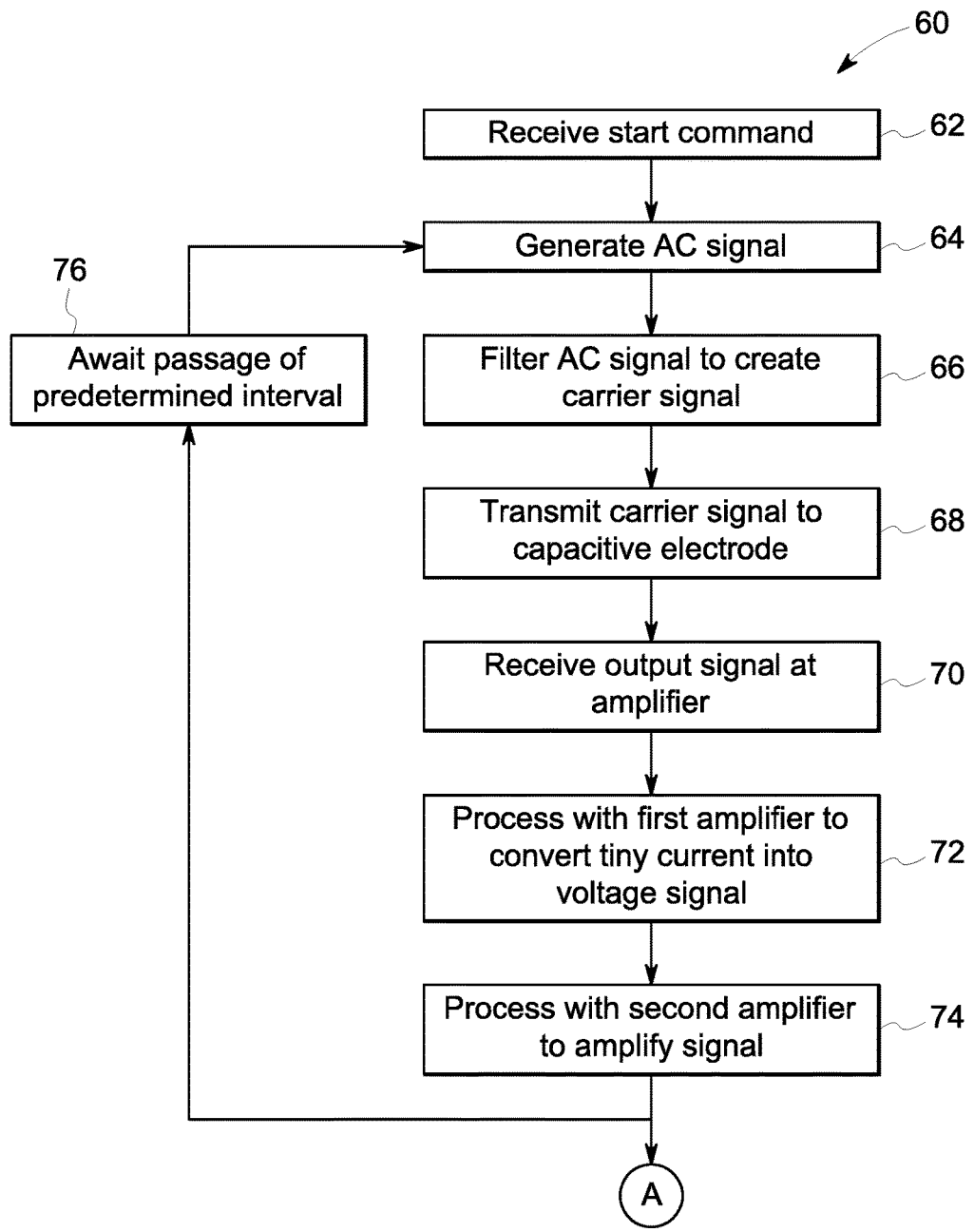
FIGS. 4A-4C depict other embodiments of a method of patient monitoring using at least one capacitive electrode.
Figure 4B:
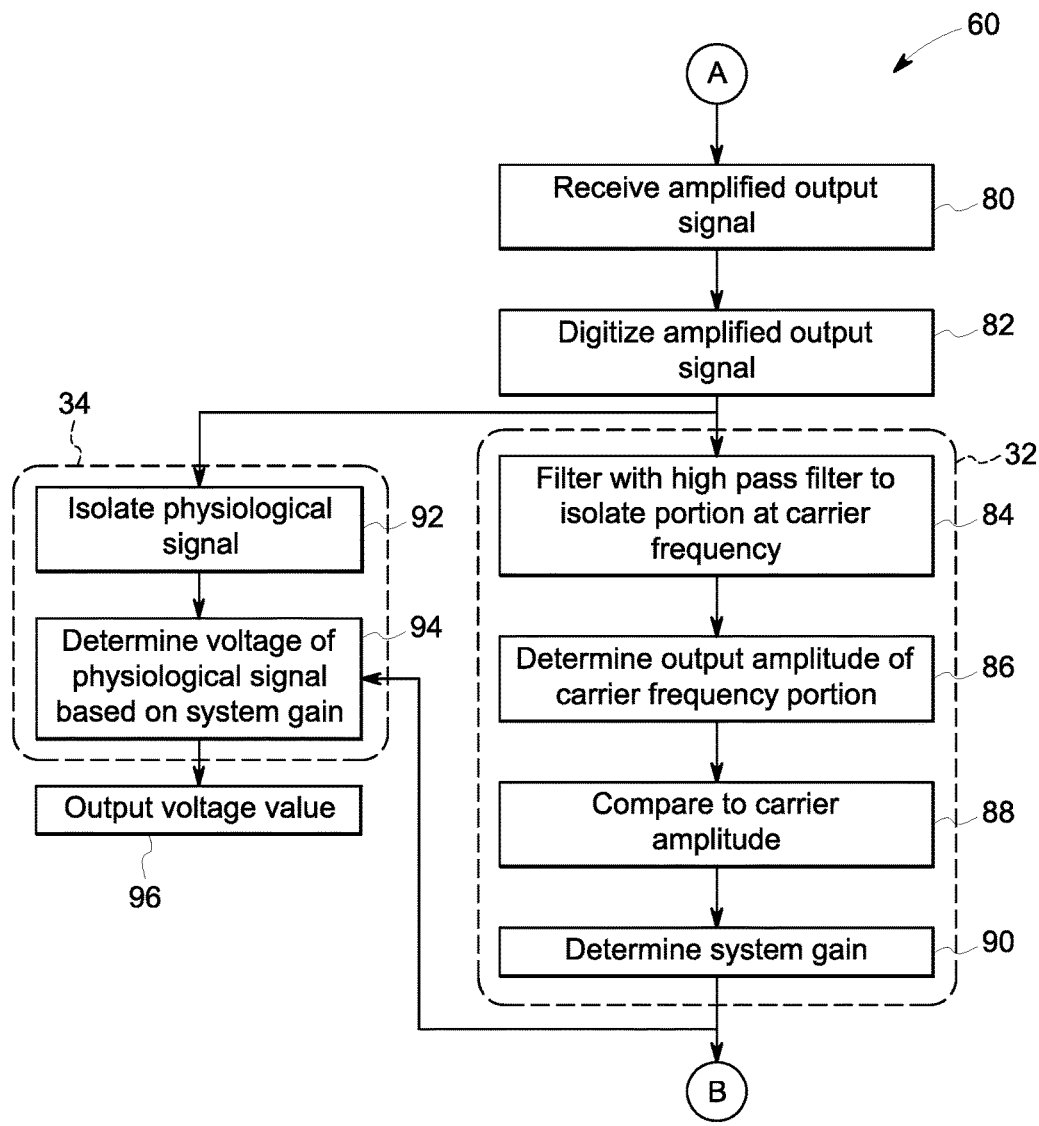

In the depicted embodiment, the computing system 200, and specifically the gain determination module 32 and the voltage determination module 34 receive the amplified output signal 28 and process the amplified output signal 28 as described herein. Additional information is received or otherwise inputted and stored within the computing system 200 to form the basis of the system gain determination, including information regarding the carrier amplitude 14, carrier frequency 15, the known amplifier gain 21 of the amplifier unit 20, and/or the filter capacitance 17. Additionally, information may be stored regarding a filter capacitor $C_c$ value, which may be utilized to calculate a capacitance of the capacitive electrode $C_e$, as is described in more detail below. FIGS. 3 and 4A-4B depict various embodiments of a method 60 that may be executed by the patient monitoring system 1, such as by the gain determination module 32 and the voltage determination module 34.

In FIG. 3, a method 60 of patient monitoring using at least one capacitive electrode includes transmitting the carrier signal to the capacitive electrode $C_e$ at step 68. An amplified output signal is received at step 80, such as from amplifier unit 20. A system gain is determined at step 90 based on an output amplitude of a carrier frequency portion of the amplified output signal. Instructions are then executed at step 94 to utilize the system gain to determine a voltage of the physiological signal.

Figure 4C:
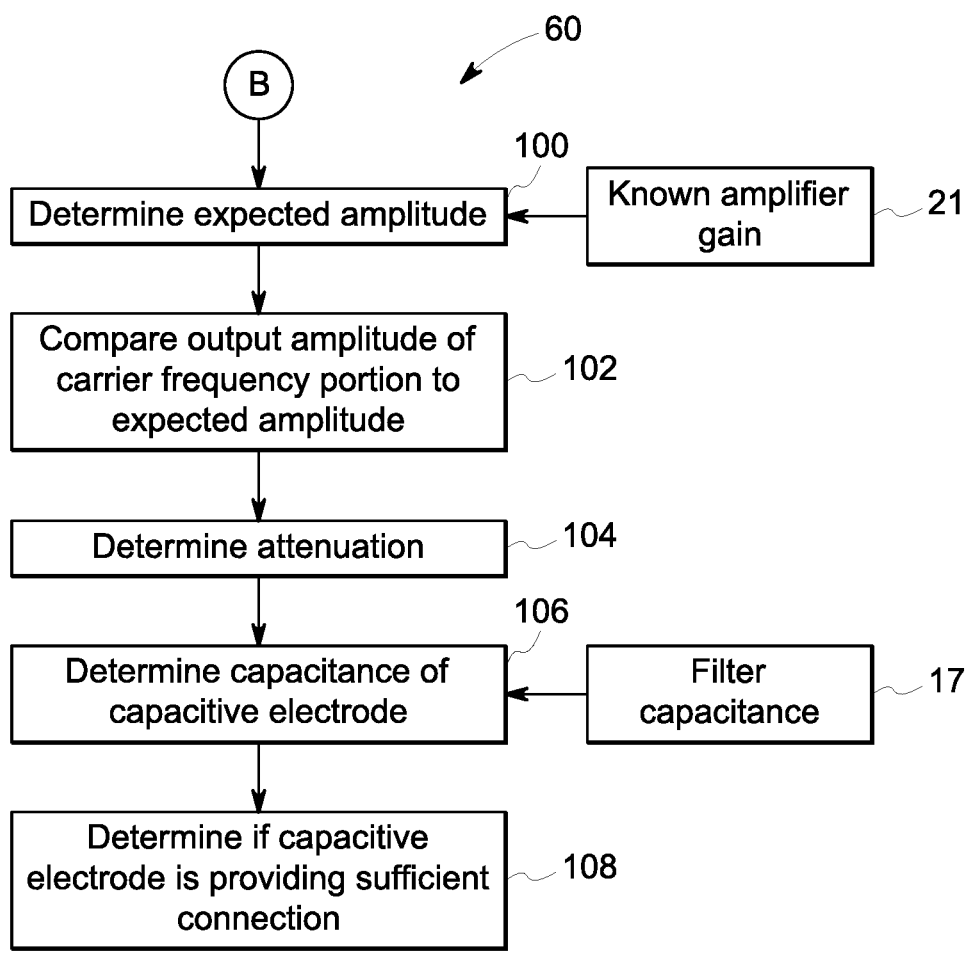

FIGS. 4A through 4C depict exemplary steps which may be executed, in part or in whole, to carry out determination of the system gain 33 and the voltage 36 of the physiological signal 40. In FIG. 4A, the method 60 begins when a start command is received at step 62. For example, the start command may be received by a clinician or other user once the capacitive electrode $C_e$ is connected to the patient 4 and ready for measurement to begin. An AC signal is generated at step 66 to create a carrier signal, such as by the capacitor $C_c$ creating a high pass filter. Step 70 represents receiving an output signal at an amplifier in the amplifier unit 20. The output signal is processed with the first amplifier 23 at step 72 to convert the tiny current of the AC output signal from the capacitive electrode $C_e$ into a voltage signal. The output of the first amplifier 23 is then processed with the second amplifier 25 to amplify the output signal at step 74. The amplified output signal is then transmitted for further processing as described herein.

The AC carrier signal may be generated at a predetermined interval, represented at step 76 as awaiting the passage of the predetermined interval before the carrier signal is generated again so that a new system gain 33 can be determined for that interval. For example, the interval for generating the carrier signal, and thus determining the system gain, may be every minute, every ten minutes, etc. In other embodiments, the carrier signal may be generated continuously and the frequency of the gain determination may be limited only by the processing ability and/or sampling rate of the system.

The amplified output signal is received at step 80 from the amplifier unit 20. In one embodiment, the amplified output signal is digitized at step 82, and the digitized signal is passed to the gain determination module 32 and the voltage determination module 34. In other embodiments, additional analog filtering may occur before digitization. In such an embodiment, separate signals may be digitized for each of the gain determination module 32 and the voltage determination module 34. In the depicted embodiment, steps are executed within the gain determination module 32 to process output signal with a high pass filter to isolate the portion of the amplified output signal 28 at the carrier frequency 15, and such steps are represented at step 84. For example, the high pass filter may have a cut off frequency just below the carrier frequency. Additionally, the filter may be a band pass filter which eliminates frequencies above the carrier frequency 15. An output amplitude of the carrier frequency portion of the output signal is determined at step 86. The output amplitude is then compared to the carrier amplitude at step 88, and a system gain is determined at step 90.

The system gain is then used to determine a voltage of the physiological signal. Namely, due to gain variance from the capacitive electrode $C_e$, the system gain must be regularly determined in order to be able to interpret the physiological signals measured from the capacitive electrodes $C_e$. Thus, the voltage determination module 34 isolates the physiological signal from the output signal at step 92, such as by applying a low pass filter with a cut off frequency just above the highest relevant frequency at which the physiological signals are expected. The voltage of the physiological signal is then determined at step 94 based on the system gain. For example, the voltage amplitude of the physiological signal may be divided by the system gain. The determined voltage value 36 is then outputted at step 96, which may be presented to a clinician via a user interface display, stored in a medical record for the patient 4, etc.

In certain embodiments, it may also be beneficial or even required to determine a capacitance value for the capacitive electrode $C_e$. For example, if the amplifier unit 20 is such that the gain is not the same for the carrier signal and the physiological signal—e.g., the gain behavior is different at high frequencies than low frequencies—then determining the capacitance of the capacitive electrode $C_e$ may be necessary in order to accurately depict the physiological signal.

FIG. 4C depicts one example of such a method. An expected amplitude is determined at step 100, which is the amplitude of the carrier signal that is due to the amplifier unit 20 alone—i.e., if the capacitive electrode $C_e$ provided no attenuation or gain change in the system. Thus, the expected amplitude requires that the gain of the amplifier unit 20 is known, which is the known amplifier gain 21. The expected amplitude is thus determined as the carrier amplitude 14 multiplied by the known amplifier gain 21. The output amplitude of the carrier frequency portion (e.g. calculated at step 86) is then compared to the expected amplitude at step 102. An attenuation amount is then determined at step 104 based on that comparison. Namely, the comparison allows determination of the gain amount attributable to the capacitive electrode $C_e$, which is likely a negative gain, or attenuation.

A capacitance of the capacitive electrode $C_e$ is then determined at step 106. This requires knowing the filter capacitance 17 of the high pass filter in the signal generator 10, which in the depicted embodiment is the capacitance of capacitor $C_c$. If the filter capacitance is known, then the capacitance of the capacitive electrode $C_e$ can be determined based on the voltage divider equations. Namely, the capacitance of the capacitive electrode $C_e$ may be calculated as:

$$C_e = \frac{V_{out} \times C_f}{V_{in} - V_{out}}$$

where the $V_{in}$ is the voltage of the carrier signal, or the carrier amplitude, and $V_{out}$ is the output amplitude of the carrier frequency portion of the amplified output signal. $C_f$ is the filter capacitance 17, which is creating the voltage divider with the capacitive electrode $C_e$. In the depicted embodiment the filter capacitance $C_f$ the value of the capacitor $C_c$.

In certain embodiments capacitance of the capacitive electrode $C_e$ can also be used to determine if the capacitive electrode $C_e$ is providing sufficient connection to the patient 4 in order to allow for obtaining clinical quality signals. If the connection to the patient 4 is too weak, such as if the capacitance is too high, then the physiological signal will not be sufficiently discernable from the noise recorded at the capacitive electrode $C_e$. Thus, steps may be executed at step 108 to determine if the capacitive electrode $C_e$ is providing a sufficient connection to the patient 4 so that quality physiological signals can be recorded from the patient 4. For example, the system may determine whether the capacitance of the capacitive electrode $C_e$ is too small, such as below a predetermined capacitance level. In such an embodiment, notification may then be provided to a clinician or other operator that physiological signals are unable to be obtained from the capacitive electrode $C_e$ due to excess noise.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

I claim:

1. A patient monitoring system comprising:
   a capacitive electrode connectable to a patient to detect an output signal;
   a signal generator unit that transmits a carrier signal to the capacitive electrode, the carrier signal having a carrier frequency and a carrier amplitude;

an amplifier unit that that amplifies the output signal detected by the capacitive electrode to generate an amplified output signal;

a gain determination module that:
   determines an output amplitude of a carrier frequency portion of the amplified output signal;
   determines a system gain based on a comparison between the output amplitude and the carrier amplitude;

a voltage determination module that:
   filters the output signal to isolate a physiological signal detected from the patient; and
   determines a voltage of the physiological signal based on the system gain.

2. The patient monitoring system of claim 1, wherein the voltage of the physiological signal is determined by dividing an amplitude of the physiological signal by the system gain.

3. The patient monitoring system of claim 1, wherein the amplifier unit:
   applies a known amplifier gain to the output signal, and wherein the gain determination module determines an expected amplitude by multiplying the carrier amplitude by the known amplifier gain;
   determines an attenuation amount of the carrier amplitude due to the capacitive electrode by comparing the output amplitude to the expected amplitude; and
   determines an electrode capacitance between the capacitive electrode and the patient based on the attenuation amount.

4. The patient monitoring system of claim 3, wherein the signal generator unit includes a filter to remove low frequencies from the carrier signal prior to transmitting it to the capacitive electrode.

5. The patient monitoring system of claim 4, wherein the gain determination module determines the electrode capacitance based on a known filter capacitance of the filter.

6. The patient monitoring system of claim 1, wherein the voltage determination module filters the output signal with a low pass filter having a cut off frequency of 150 Hz or lower.

7. The patient monitoring system of claim 6, wherein the carrier frequency is greater than 150 Hz.

8. The patient monitoring system of claim 1, wherein the carrier frequency is at least 1 kHz.

9. The patient monitoring system of claim 8, wherein the carrier frequency is at least 50 kHz.

10. The patient monitoring system of claim 1, wherein the system gain is determined at a predetermined interval by generating the carrier signal at that interval.

11. A method of patient monitoring using at least one capacitive electrode, the method comprising:

generating a carrier signal at a carrier frequency and carrier amplitude;

transmitting the carrier signal to a capacitive electrode attached to a patient;

receiving an output signal from the capacitive electrode;

amplifying the output signal to create an amplified output signal;

determining an output amplitude of a carrier frequency portion of the amplified output signal;

comparing the carrier amplitude to the output amplitude to determine a system gain;

filtering the output signal to isolate a physiological signal of the patient; and determining voltage of the physiological signal based on the system gain.

12. The method of claim 11, wherein the voltage of the physiological signal is determined by dividing an amplitude of the physiological signal by the system gain.

13. The method of claim 11, wherein amplifying the output signal includes applying a known amplifier gain to the output signal, and further comprising:
   determining an expected amplitude by multiplying the carrier amplitude by the known amplifier gain;
   determining an attenuation amount of the carrier amplitude due to the capacitive electrode by comparing the output amplitude to the expected amplitude; and
   determining an electrode capacitance between the capacitive electrode and the patient based on the attenuation amount.

14. The method of claim 13, further comprising filtering the carrier signal with a high pass filter prior to transmitting it to the capacitive electrode, wherein the high pass filter at least removes frequencies below 150 Hz.

15. The method of claim 14, wherein the electrode capacitance is determined based on a known filter capacitance of the high pass filter.

16. The method of claim 11, wherein the step of filtering the output signal to isolate the physiological signal includes filtering the output signal with a low pass filter with a cut off frequency of 150 Hz.

17. The method of claim 11, wherein the carrier frequency is greater than 150 Hz.

18. The method of claim 17, wherein the carrier frequency is at least 1 kHz.

19. The method of claim 18, wherein the carrier frequency is at least 50 kHz.

20. The method of claim 11, wherein the system gain is determined at a predetermined interval and the carrier signal is generated at that interval.

* * * * *